United States Patent [19]

Poulsen

[11] 4,192,309
[45] Mar. 11, 1980

[54] INHALATION DEVICE WITH CAPSULE OPENER

[75] Inventor: Boyd J. Poulsen, Palo Alto, Calif.

[73] Assignee: Syntex Puerto Rico, Inc., Humacao, P.R.

[21] Appl. No.: 939,614

[22] Filed: Sep. 5, 1978

[51] Int. Cl.$^2$ ..................... A61M 15/06; A61M 15/08
[52] U.S. Cl. ............................. 128/203.15; 128/272; 215/DIG. 3; 206/38; 7/170; 131/170 R
[58] Field of Search ............... 128/266, 265, 206, 208, 128/272, 232; 7/169, 170; 215/305, DIG. 3; 206/38; 131/170 R

[56] References Cited

U.S. PATENT DOCUMENTS

| | | | |
|---|---|---|---|
| 2,587,215 | 2/1952 | Priestly | 128/206 |
| 2,655,259 | 10/1953 | Davoren | 206/38 X |
| 3,858,583 | 1/1975 | Hallworth et al. | 128/266 |
| 4,098,273 | 7/1978 | Glenn | 128/266 X |

*Primary Examiner*—Henry J. Recla
*Attorney, Agent, or Firm*—Tom M. Moran; Joseph I. Hirsch

[57] ABSTRACT

A breath-actuated inhalation device for dispensing a powdered medicament from a powdered medicament-holding capsule, comprising an elongate housing having a passageway for the movement of air therethrough, one end of the housing being an output end adapted for insertion into a user's mouth or nasal passage, the passageway having an inlet end terminating in an emptying chamber at the output end of said housing, the cross-sectional area of the passageway being less than the cross-sectional area of the emptying chamber, and means associated with said housing for receiving a powdered medicament-holding capsule. A collar surrounds at least a portion of the periphery of the housing adjacent the emptying chamber and has at least one substantially flat surface with a notch therein, which allows a first, smaller part of a two-part capsule to fit therein but which is too small to allow the second, larger part of the capsule to fit therein. When the smaller, first part of the capsule is placed within the notch with the leading edge of the larger, second part of the container contacting said flat surface of said collar, and the first part is pulled away from the second part, the capsule is opened by virtue of the second larger part being retained by said flat surface.

1 Claim, 5 Drawing Figures

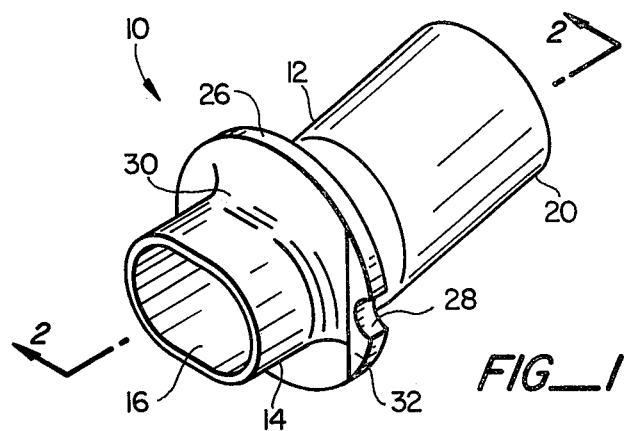
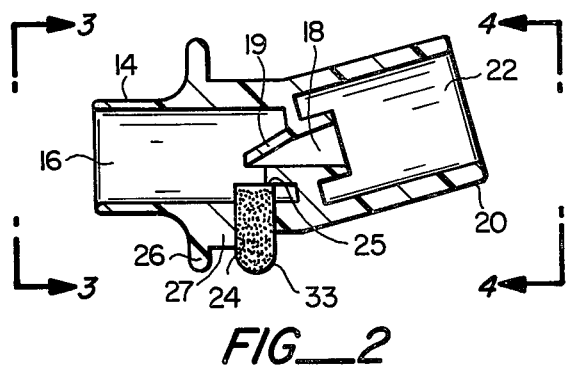
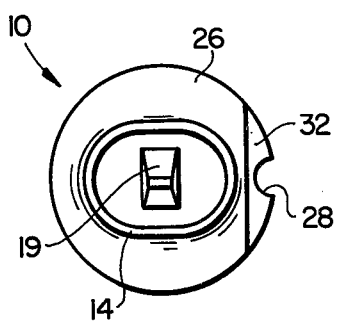
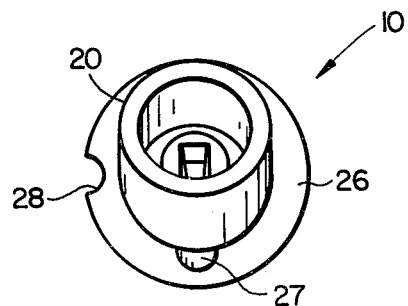
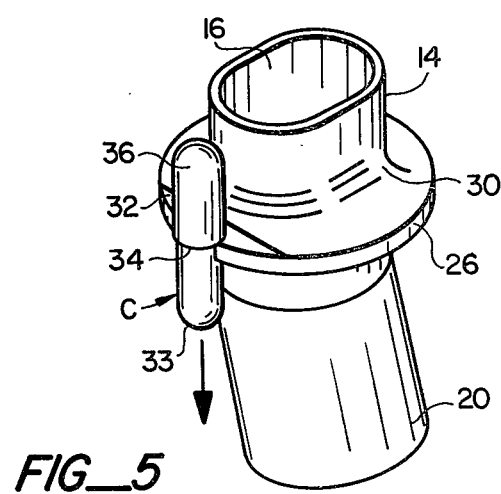

INHALATION DEVICE WITH CAPSULE OPENER

FIELD OF THE INVENTION

This invention relates to a device for the administration of a powdered medicament by inhalation. More particularly, this invention relates to an inhalation device having no parts which move while the medicament is dispensed and further having means to open the capsule prior to insertion of the capsule into the device.

BACKGROUND OF THE INVENTION

Known prior art inhalation devices include, for example, those shown in U.S. Pat. Nos. 3,938,516; 3,964,483; 3,973,566; and 4,005,711. In all of these devices a capsule containing a powdered medicament is first opened and then inserted into an opening in the device and held either by friction fit or by the finger pressure of the user. In opening the capsule, however, it is difficult to hold the device in one hand while taking the capsule apart with the other. Usually the user must put the device down and then use both hands to take the capsule apart. Thereafter he must pick up the device and insert the capsule into the appropriate opening. Other devices have been proposed which employ means for opening the capsule after it is inserted into the inhalation device, see for example U.S. Pat. No, 4,014,336. However, with these devices the user sometimes runs the risk of leaving the portion of the capsule that has been removed (generally the top portion of the capsule) within the device thereby possibly adversely affecting the delivery of the powder during inhalation.

With the instant invention, the chance of leaving a portion of the capsule within the device after opening the capsule is eliminated. Further, opening the capsule and inserting the capsule into the device is readily accomplished without havng to put down the device.

BRIEF DESCRIPTION OF THE DRAWINGS AND DESCRIPTION OF THE INVENTION

Features and advantages of the present invention will become more apparent from the following detailed description, taken together with the accompanying drawings wherein:

FIG. 1 is a perspective view of the inhalation device of the present invention showing the capsule opening means;

FIG. 2 is a cross-sectional view of the inhalation device of FIG. 1 taken along line 2—2 of FIG. 1 showing the device of the invention ready for inhalation;

FIG. 3 is a front-end view taken along line 3—3 of FIG. 2;

FIG. 4 is a read-end view taken along line 4—4 of FIG. 2.

FIG. 5 is a perspective view of the inhalation device of the present invention wherein a capsule is positioned to be opened using the improvement of this invention.

In the discussion below, reference will be made to a two-part gelatin capsule as the exemplary container for presenting the medicament to the device for administration. As set forth below, other containers are contemplated for use with the device described herein.

Referring first to FIG. 1, there is shown an inhalation device 10 having an elongated housing 12 which may be of cyclindrical cross-section, eliptical cross-section, or a combination of the two. As depicted in FIGS. 1–5, part of the housing is cylindrical while the other part (the mouthpiece) may be eliptical in transverse cross-section. At one end of housing 12 is mouthpiece 14 for insertion into the mouth or nasal passages of a user thereof. Mouthpiece 14 can be designed to permit insertion directly into a nasal passage or, if desired, an adapter (not shown) can be placed over the mouthpiece to permit nasal use. Adjacent mouthpiece 14 is an emptying chamber 16 connected at the inner end thereof to passageway 18 which extends to the inlet end 20 of the device and communicates with inlet chamber 22. The manner of connecting passageways 18 with chamber 16 and 22 can be as shown or more streamlined, if desired, as long as the particular configuration selected is effective to cause the powdered medicament to be expelled from capsule C during the desired number of inhalations. Other exemplary embodiments for the device are shown in U.S. Pat. Nos. 3,938,516 to Mathes; 3,964,483 to Mathes; 3,973,566 to Mathes; and 4,005,711 to Glenn, which are incorporated herein by reference.

The housing 12 may be of such design that the longitudinal axes of passageway 18 and chambers 16 and 22 are substantially the same and are parallel. Alternatively, the longitudinal axis of passageway 18 may be slightly offset, for example at an angle of about 5° to 30°, preferably about 15°, from the longitudinal axis of the emptying chamber 16, for example as is best seen in FIG. 2 hereof.

Adjacent the lower, inner portion of chamber 16, there are means for receiving a medicament-containing capsule C. In FIG. 2 the capsule receiving means is an opening 24 which extends from the outer portion of the device to chamber 16 situated just below deflector means 19. The opening is generally of a dimension which is sufficient to allow capsule C to fit within the opening and be retained therein by a friction fit. To aid in guiding capsule C into opening 24, extension 27 is positioned adjacent opening 24. Extension 27 has a curvature complementary to capsule C so that the capsule is easily guided into opening 24. Capsule C, as it is being inserted into opening 24, eventually comes into contact with stop 25 which properly places the top of the opened capsule relative to deflector 19.

Inhalation device 10 is equipped with collar 26 which extends around the periphery of the outside of the device. The collar may extend entirely around the periphery or only part way. It is designed to prevent the patient from inhaling the entire device, to provide proper positioning of the device within the mouth, and also to provide for the capsule opening means. The capsule opening means is a notch 28 in collar 26. The notch is of a dimension which is sufficiently small to allow the smaller part of a two-part capsule to fit therein, but which is too large to allow the second and larger half of the capsule to fit therein or be pulled therethrough. Thus, when the smaller half is placed in the notch (as is best seen in FIG. 5) and pulled downwardly in the direction of the arrow, the upper half of the capsule is prevented from moving downwardly and, accordingly, is pulled off of the lower capsule half as movement continues. At least that portion of the collar adjacent the notch should be flat so that the larger capsule half will be readily retained thereon without tilting as the capsule is being opened. If the surface is slanted, not enough pressure can be put on the upper half of the capsule to easily remove it from the lower half of the capsule. Thus, as shown in FIGS. 1 and 5, collar 26 has a rounded intersection 30 with mouthpiece 14 and has flat surface 32 (adjacent notch 28) against which the larger part of the capsule is retained during the opening process.

Thus, in operation, the user of the inhalation device merely holds the smaller part 33 of the capsule C in one hand between the thumb and forefinger, ease that part into notch 28, brings the overhanging edge 34 of the larger portion 36 of capsule C into contact with flat surface 32 of collar 26, and pulls downwardly while holding onto the inhalation device with the other hand. Once the upper portion 36 of capsule C is removed, the lower portion 33 is fitted into opening 24 as shown in FIG. 2, the user places the mouthpiece in his mouth and inhales. The air enters chamber 22, goes through passageway 18 until it hits deflector 19 where it is deflected into portion 33 of the capsule holding the powdered medicament. The deflector can be arranged at different positions as long as a sufficient portion of the air stream is deflected into the capsule to cause the powdered medicament to be dispensed therefrom. Upon inhalation, the air passing through the device, including the portion deflected into the capsule, promptly and effectively causes the powdered medicament to be expelled from the capsule and entrained in the air stream passing through the device and, as such, carried into the throat, nasal passages or lungs of the user thereof for beneficial or therapeutic action thereof to occur.

The physical properties of each medicament formulation (i.e., the ability to fluidize and the flow characteristics thereof) will affect the ease or manner in which it is dispensed with these or other inhalation devices. However, for a given powdered formulation, varying the diameter of passageway 18, the positioning of opening 24 (from the position as shown toward the open end of chamber 16), the angle of the deflector 19, the depth to which the deflector 19 extends above or below the longitudinal axis of passageway 18, the height above the inside of emptying chamber 16 to which the medicament-holding container extends, and/or, in general, modification of the overall configuration and shape of chamber 16 and passageway 18, devices can be made to deliver the medicament in a different number of inhalations or in a longer or shorter period of time, depending upon the nasal or lung capacity and strengths of each particular user. Quite obviously, no single device will be optimal for all persons requiring administration of powdered medicaments since, for example, people with differing lung capacities and strengths are known to generate flow rates from about 30 liters/minute or so to about 120 liters/minute or so through inhalation devices of this and known types. Nonetheless, the devices of this invention afford such variability through proper selection of the various design parameters listed above, that a device, embraced within the scope of this disclosure, can be designed for a particular patient-generated flow rate to deliver the medicament according to a certain set of pre-determined objectives (e.g., slow or fast adminstration, one or more inhalations, etc.). The net result is that a family of devices, all embraced within the present disclosure, can be designed, each of which will deliver the medicament under a different, given set of selected administration conditions. Conversely, the devices hereof can be designed to cover an extensive range of operating conditions and thus be suitable for use by a variety of persons having differing inhalation capabilities or capacities.

While the present invention has been described with reference to specific embodiments thereof, it will be understood by those skilled in this art that various changes may be made and equivalents may be substituted without departing from the true spirit and scope of the invention. Additionally, other modifications may be made to adapt a particular situation, material or composition of matter, structural desirability, or then-present objective to the spirit of this invention without departing from its essential teachings.

What is claimed is:

1. A breath-actuated inhalation device for dispensing a powdered medicament from a powdered medicament-holding container, which device comprises an elongate housing having a passageway for the movement of air therethrough, one end of said housing being an output end adapted for insertion into the mouth or nasal passage of a user thereof, the passageway having an inlet end terminating in an emptying chamber at the output end of said housing, the cross-sectional area of the passageway being less than the cross-sectional area of the emptying chamber, means associated with said housing for receiving a powdered medicament-holding container, a collar which surrounds at least a portion of the periphery of said housing adjacent the emptying chamber, said collar having at least one substantially flat surface thereon, and a notch within said flat surface of said collar, the notch being of such a size to allow a first, smaller part of a two-part medicament-holding container to fit therein but which is too small to allow the second, larger part of the medicament-holding container to fit therein, whereby when the smaller, first part is placed within the notch with the leading edge of the larger, second part of the container contacting said flat surface of said collar, and the first part is pulled away from the second part, the medicament-holding container is opened by virtue of the second larger part being retained by said flat surface.

* * * * *